US00PP17220P3

(12) United States Plant Patent
Moon

(10) Patent No.: US PP17,220 P3
(45) Date of Patent: Nov. 21, 2006

(54) **JAPANESE *ZELKOVA* TREE NAMED 'ZSFKF'**

(50) Latin Name: *Zelkova serrata*
Varietal Denomination: ZSFKF

(75) Inventor: Dwayne C. Moon, Loganville, GA (US)

(73) Assignee: Southern Selections, LLC, Loganville, GA (US)

( * ) Notice: Subject to any disclaimer, the term of this patent is extended or adjusted under 35 U.S.C. 154(b) by 466 days.

(21) Appl. No.: 10/295,228

(22) Filed: Nov. 15, 2002

(65) Prior Publication Data

US 2004/0098773 P1 May 20, 2004

(51) Int. Cl.
*A01H 5/00* (2006.01)

(52) U.S. Cl. ..... Plt./216

(58) Field of Classification Search ..... Plt./216
See application file for complete search history.

*Primary Examiner*—Anne Marie Grunberg
(74) *Attorney, Agent, or Firm*—Polster, Lieder, Woodruff & Lucchesi, L.C.

(57) ABSTRACT

A Japanese *Zelkova* tree (*Zelkova serrata*) named 'ZSFKF' having a broad-spreading habit, fibrous root system, a more rapid growth rate, and heat tolerance and also capable of being reproduced reliably from vegetative cuttings.

7 Drawing Sheets

BACKGROUND OF THE INVENTION

The present invention relates to a new and distinct variety of *Zelkova serrata,* Japanese *Zelkova* tree, which I have given the cultivar name 'ZSFKF'.

DISCOVERY

I discovered my new tree in the spring of 1989 growing in a production field at Pritchard's Tree Farm in Madison, Morgan County, Ga., among a group of cultivated Japanese *Zelkova* trees. This particular area of Morgan County has a clay loam soil type, is located in USDA Hardiness Zone 7 and receives average yearly rainfall of 50 inches. This tree was acquired from a nursery in McMinnville, Tenn. in a grouping of 'Village Green' and 'Green Vase' *Zelkova* liners in the spring of 1986. It was apparent at a very early age that 'ZSFKF' was unique due to the vigorous growth rate and broad structure when compared to these known cultivars in the same field.

PROPAGATION

'ZSFKF' was asexually propagated at my direction in the spring of 1993 by means of softwood cuttings treated with rooting hormones and held for six to eight weeks in a controlled greenhouse environment in Loganville, Ga. This propagation and resulting progeny have proven the characteristics of my new variety to be genetically stable. Furthermore, these observations have confirmed that my new variety represents a new and improved variety of Japanese *Zelkova* as particularly evidenced by the broad-spreading habit, more rapid growth rate, fibrous root system and heat tolerance which can be reliably asexually propagated.

UNIQUENESS

'ZSFKF' was observed to have broad spreading habit, more rapid growth rate, a fibrous root system and greater heat tolerance than other cultivars currently available at time of submittal. These characteristics distinguish my new tree from other typical seedling Japanese *Zelkova* and the known cultivars.

USE

'ZSFKF' was observed for a period of time and is believed to be particularly useful for residential street plantings and lawns, parks, or other large areas. The shorter mature height 'ZSFKF' would make it suitable for planting beneath power lines. The well developed root structure and rapid growth rate of my new variety will benefit growers who can produce a mature tree in less time. The heat tolerance will extend the range of Japanese *Zelkova* south and improve its survivability in areas where it can currently be grown but takes time to establish.

SUMMARY OF THE INVENTION

BACKGROUND

Japanese *Zelkova* is typically a low-branched, vase-shaped tree in youth and maturity. My new cultivar differs from the species in that is has broad spreading habit, more rapid growth rate, and heat tolerance. Japanese *Zelkova* is native to Japan, Korea, Taiwan, and Manchuria. It performs well in zones 5 to 7, and some of the cultivars will survive in Zone 4. Trees in Zones 7 and 8 will often bronze during the summer, depending on the intensity and duration of the heat during the summer. Japanese *Zelkova* has been successfully grown from Wisconsin to Rhode Island to Georgia to Texas. It prefers rich colluvial soils at the base of mountains and along streams and rivers in its native area; however, the species thrives in a variety of soils and climates once established. Japanese *Zelkova* does equally well in North Georgia's acid red clays and the high pH Kansas plains. I expect 'ZSFKF' to perform as well as typical Japanese *Zelkova* in Zones 5 to 7, and outperform typical Japanese *Zelkova* in Zone 8 and the upper part of Zone 9.

INDUSTRY REPRESENTATION

Commercially grown Japanese *Zelkova* are predominantly represented in the industry by named cultivated varieties. There are at least fifteen known cultivars including a variegated form, a weeping form, and a dwarf. Most of the remaining cultivars are described as vase-shaped, and most have been selected for cold hardiness. The two most popular cultivars are 'Village Green' and 'Green Vase'. 'Green Vase' is considered the best of the cultivars and has a distinct vase-shaped form with uprightly arching branches and a mature size of 60–70 feet tall and 40–50 feet wide (a height to width ration of 1.4 to 1.5). 'Village Green' is hardier than 'Green Vase' and has a broom-shaped mature habit and a mature size of 38'–40' tall and 38' wide (a height to width ration of 1.0 to 1.1).

After sizteen years, the current size of my new tree is 35' tall and 40' wide (a height to width ration of 0.88). In my experience, no other cultivar or seedling Japanese *Zelkova* has displayed the growth rate and heat tolerance of 'ZSFKF'. My new tree is currently 21.5" in caliper, an average annual caliper increase of 1.34". Other Japanese *Zelkova* in this area have an average annual caliper increase of about 1". This rapid growth rate appears to be due to increased heat tolerance. 'ZSFKF' has thrived through several consecutive summers of 96–100° F. Some of the progeny are currently being evaluated in central Florida and have demonstrated survivability as far south as Orlando, an area that has not been able to commercially produce Japanese *Zelkova* due to the heat and humidity.

'ZSFKF' has also demonstrated adaptability to the climate in the Southeast that has not been matched by other cultivars or seedlings. In a production setting as 1 to 2 year old plants, 'Green Vase' and 'Village Green' both have survivability problems with the early fall freezes and late spring frosts. It is not uncommon to lose up to 30% of a liner crop due to an untimely freeze. 'ZSFKF' has never been seen to suffer losses due to early or late freezes.

DESCRIPTION OF THE DRAWINGS (PHOTOGRAPHS)

In the accompanying photographs which depict the color of the tree and foliage of my new variety as nearly as is reasonably possible to make the same in a color illustration of this character;

FIG. 1, taken at Morgan County, Ga. in the summer of 2002, when the tree was 16 years old, 35 feet tall, 40 feet wide, and 21.5 inches in caliper, shows the summer habit of the initially discovered tree of my new variety showing the broad-spreading habit and dense canopy;

Figure 1:
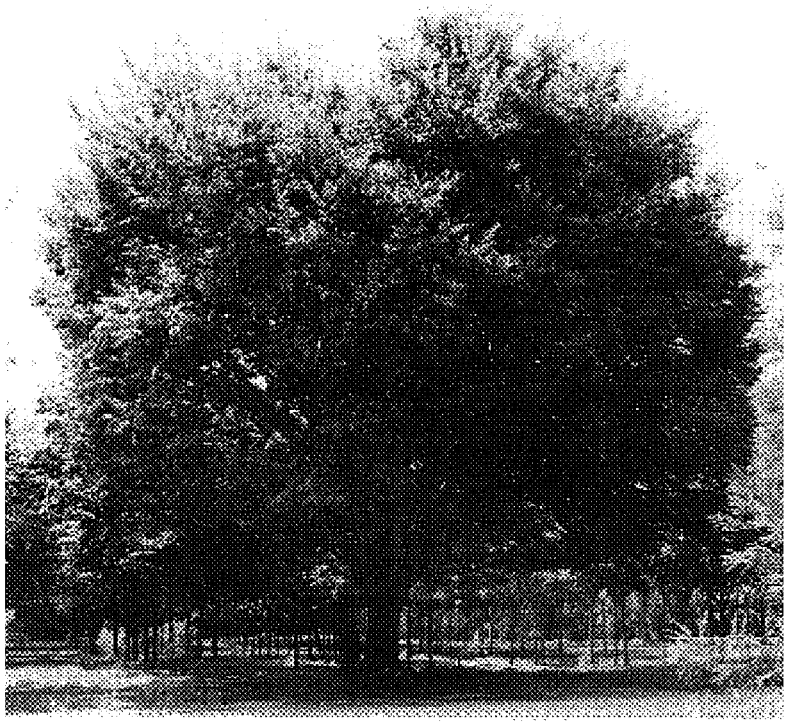
Figure 2:
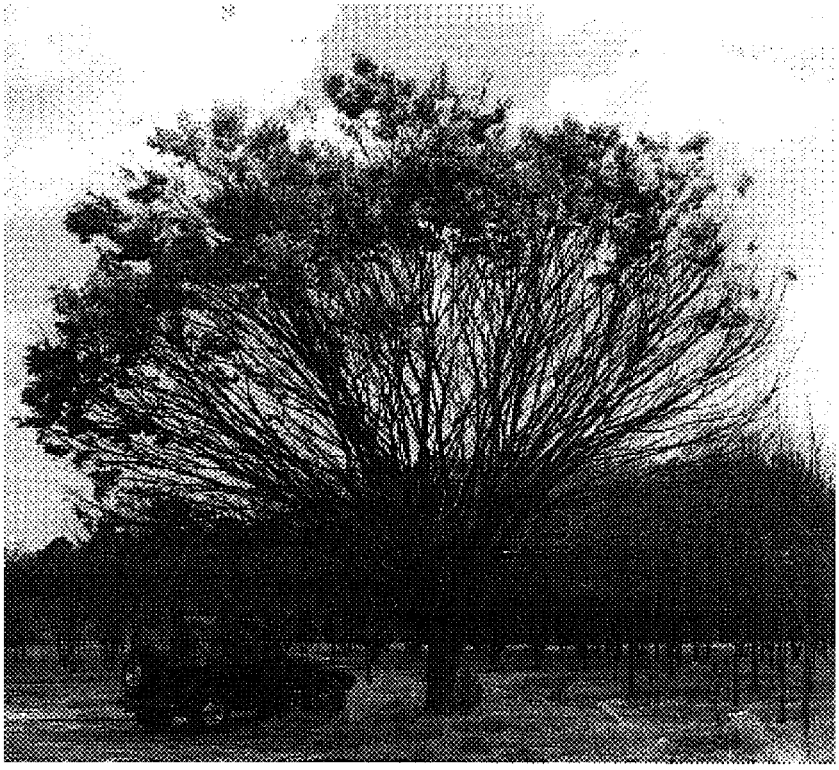
FIG. 2 shows the early spring habit of the initially discovered tree of my new variety showing the branching habit with interior branches nearly vertical, becoming more horizontal until they are nearly flat on the outer edge of the tree.
Figure 3:
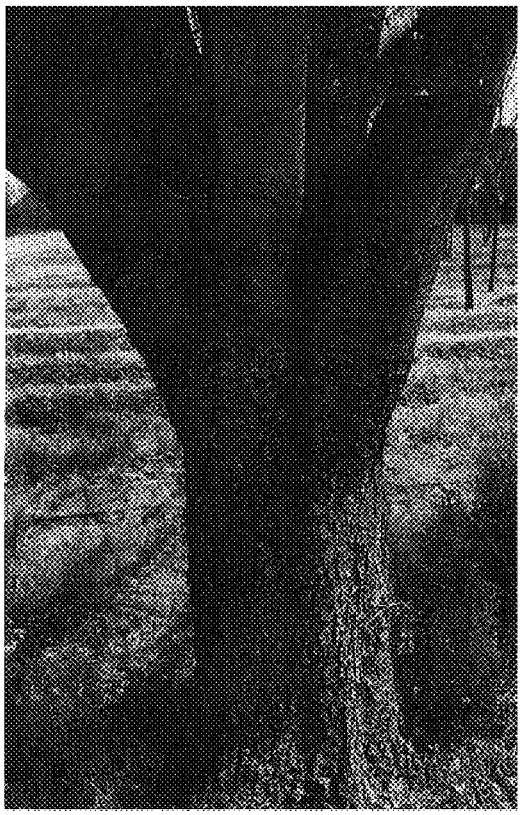
FIG. 3 shows the trunk and primary branching of the initially discovered tree of my new variety and shows the scaly nature of the main trunk.
Figure 3A:
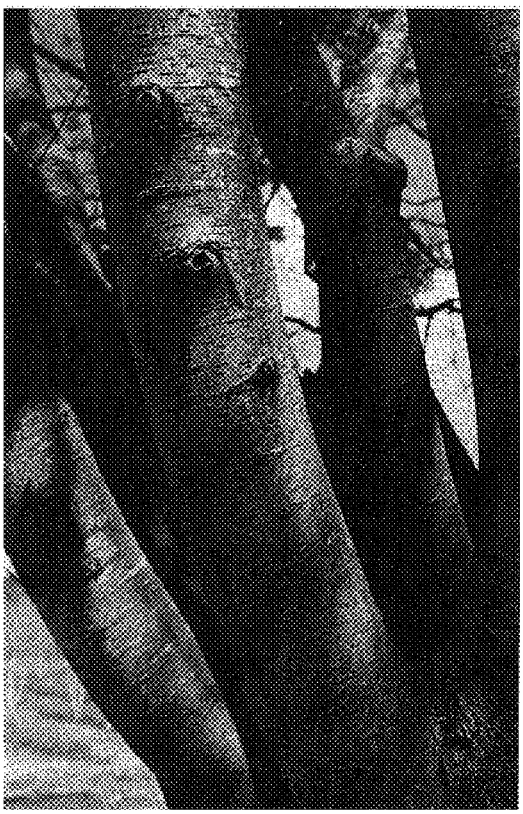
Figure 4:
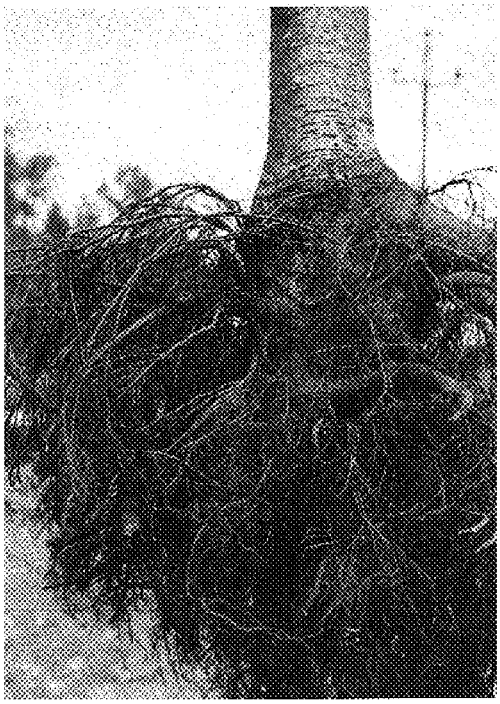
Figure 4A:
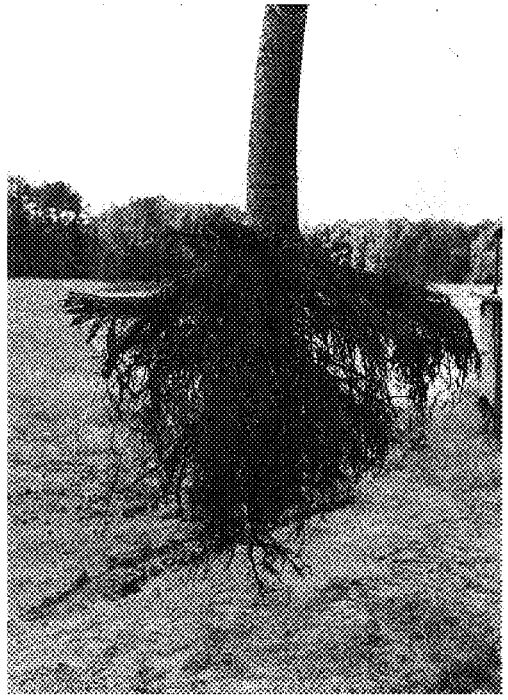
Figure 5:
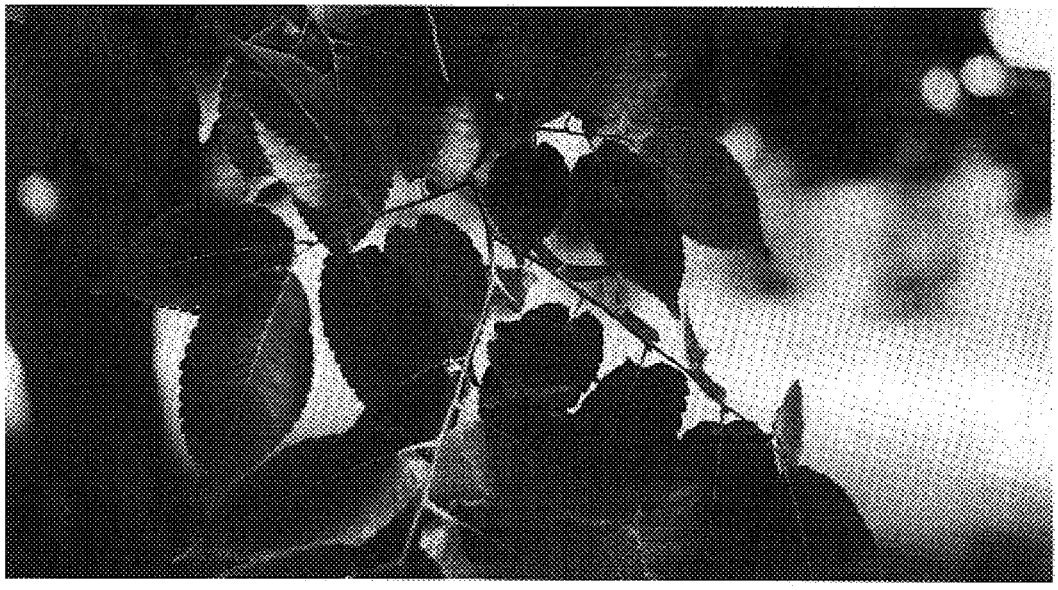
Figure 6:
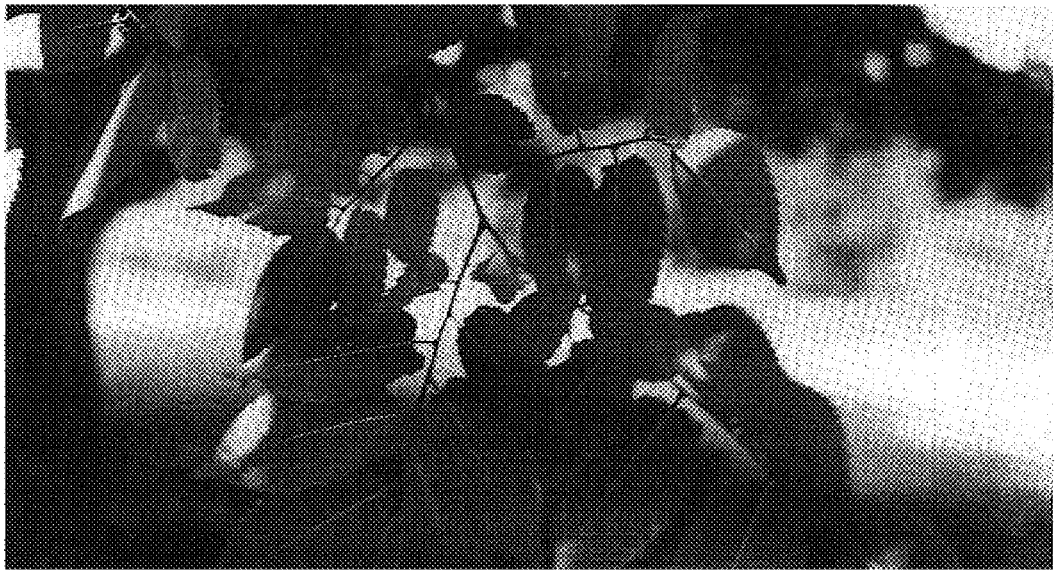
Figure 7:
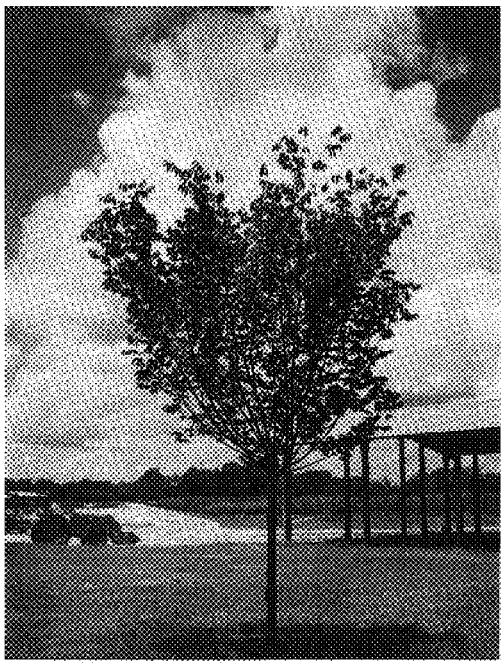
Figure 8:
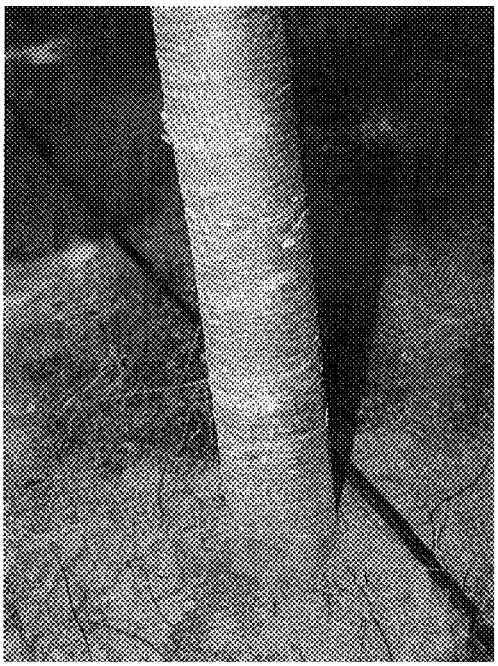
Figure 9:
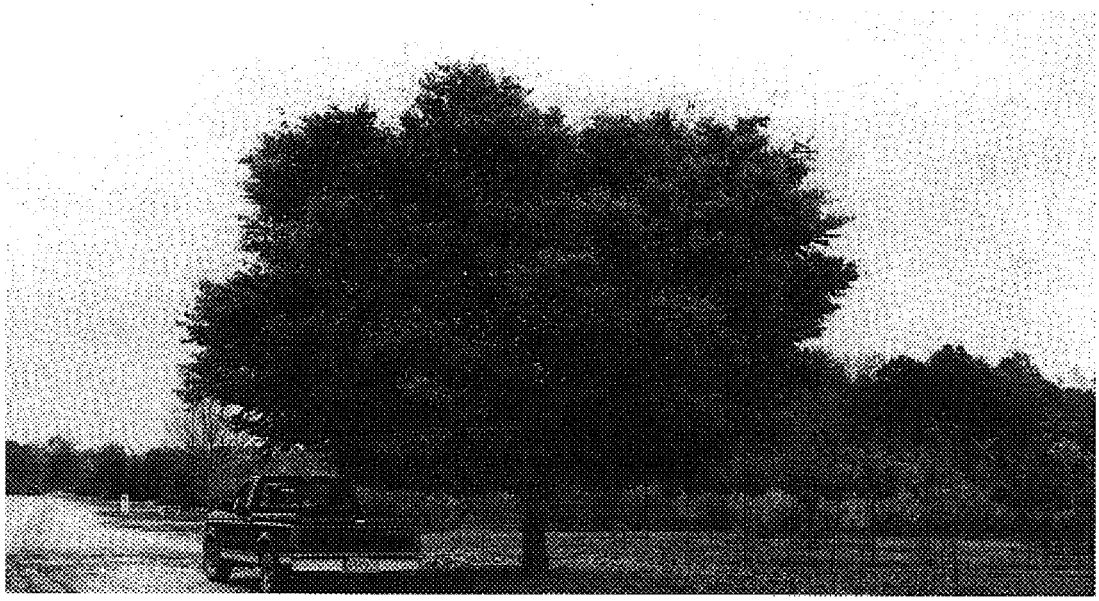
Figure 10:
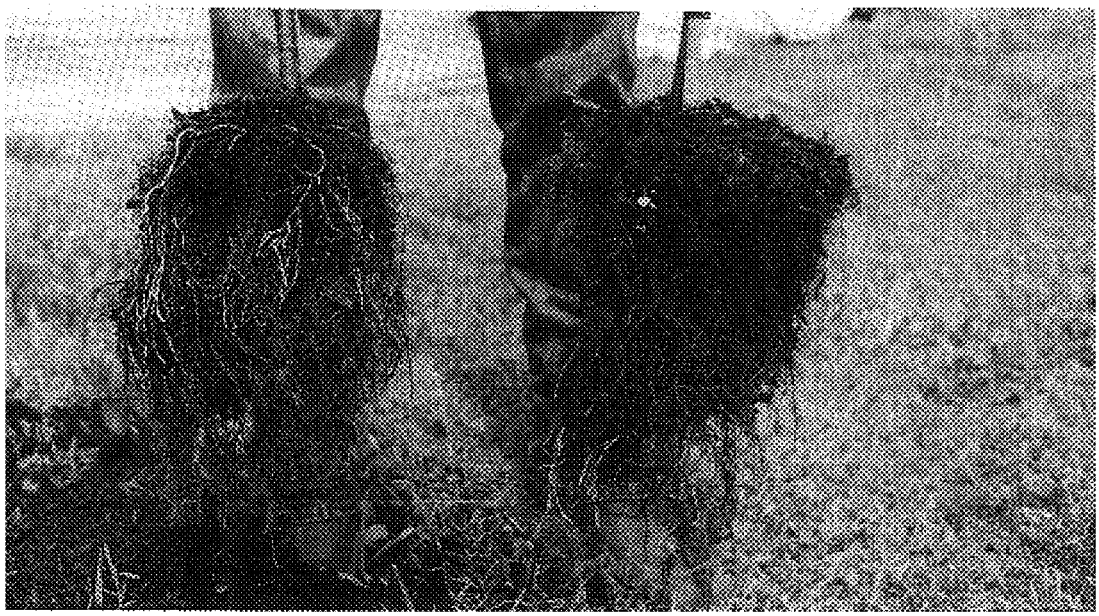
Figure 11:
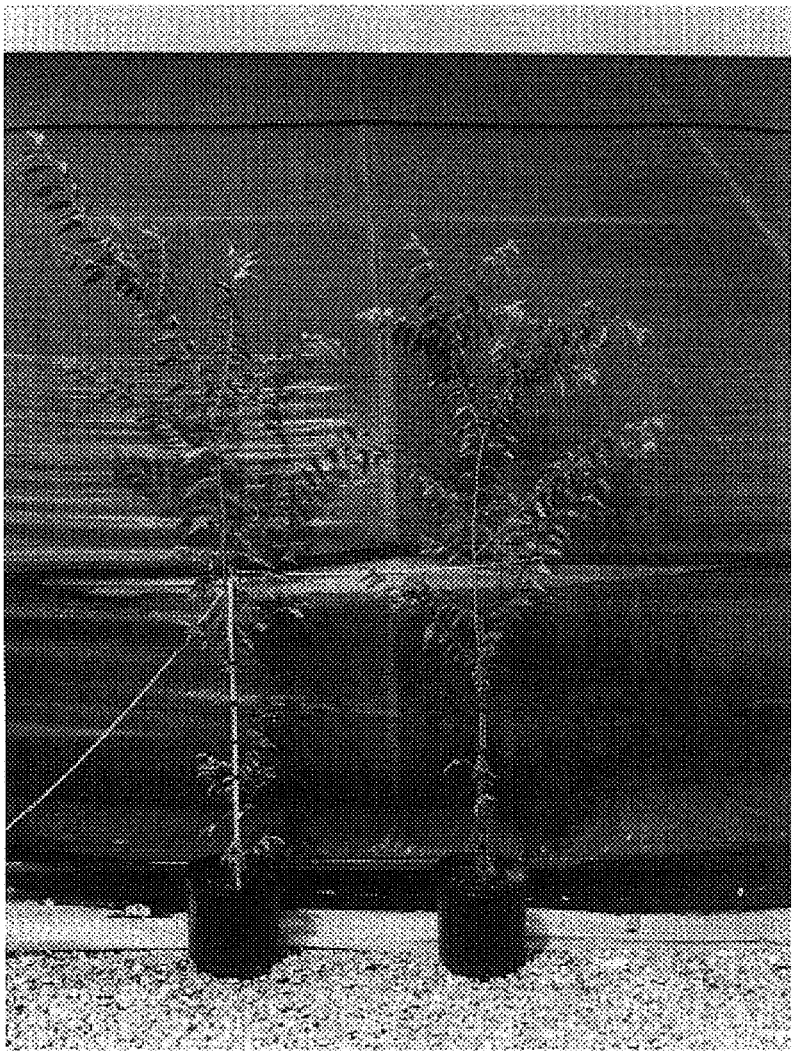

FIG. 3*a* is a photograph showing the striated pattern of the branches of the tree shown in FIG. 3;

FIGS. 4 and 4*a* depict a root system and trunk of one of the progeny showing the striated, heavily lenticelled trunk and the fibrous root system;

FIG. 5 shows the upper leaf surface of 'ZSFKF':

FIG. 6 shows the lower leaf surface of 'ZSFKF':

FIG. 7 shows a prodigy growing in Central Florida after two years;

FIG. 8 shows the trunk of a young prodigy;

FIG. 9 shows the tree of FIG. 1 at the start of fall color;

FIG. 10 was taken in late August 2002, and shows a comparison of root structure, with the tree on the left being a 'Green Vase' variety planted from a cutting in August 2001, and the tree on the right being a 'ZSFKF' variety planted from a cutting in June 2002; and FIG. 11 was taken in late August 2002, and shows a comparison of trunk and branch structure with the tree on the left being a 'Green Vase' variety planted from a cutting in August 2001 and the tree on the right is a 'ZSFKF' variety planted from a cutting in June 2002.

DETAILED DESCRIPTION

Botanical Description of the Plant

The following is a detailed description of my new variety of Japanese *Zelkova* with color terminology in accordance with The Royal Horticulture Society (R.H.S.) Colour chart except where the context indicated a term having its ordinary dictionary meaning.

My new tree has not been observed under all growing conditions and variations may occur as a result of different growing conditions. All progeny of my new variety, insofar as have been observed, have been identical in all characteristics described hereinafter. Other than as set out hereinafter, as of this time no other characteristics have been observed which are different from common Japanese *Zelkova* trees which have been observed by the inventor.

Parentage: Seedling of unknown parentage grown from bare-root liner purchased in the spring of 1986 from a nursery in McMinnville, Tenn.

Locality where grown and observed: A clay loam soil production field at Pritchard's Tree Farm in Madison, Morgan County, Ga., in USDA Hardiness Zone 7 with average yearly rainfall of 50 inches.

Leaves: Typical of the species, 'ZSFKF' consistently maintains healty foliage throughout the summer compared to other seedling and cultivar Japanese *Zelkova* which can sometimes bronze; alternate, simple, ovate to oblong-ovate, rounded or subcordate, acuminate or apiculate, sharply serrate with acuminate teeth, 2" wide by 4"; dark green above like 141B and medium green below like 141C; fall is orange-brown; petiole; green ⅛" to ¼" long.

Buds: Ovoid, acutish, with imbricate, dark brown scales, ¼" long.

Flowers: Typical of the species; not showy; male, female, and bisexual flowers on a short shoot; appear with the leaves.

Fruit: Typical of the species; small yellow-green drupe about ¼" wide, ripening in the fall.

Stem: Pubescent when young, becoming glabrous brown at maturity.

Trunk: Typical of the species, when young, gray green like 198C with swatches of gray like 201A, smooth, heavily lenticelled; developing thick scales with age and blended colors of gray like 201A and gray-brown like 177B; does not exfoliate to the same extent as some of the cultivars.

Branching: Very uprightly ascending branches, but with many wide-spreading branches which give 'ZSFKF' its width. At the center of my new tree, branches are almost perpendicular to the ground. As they move to the outside of my new tree, branching becomes almost parallel to the ground.

Growth habit: Broad-spreading.

Root system: About 25% more fibrous than some of the cultivars and many seedlings.

Vigor: In production, averages up to 1.25" in caliper and possibly more per year; has averaged 1.34" in caliper per year since it was planted as a bare-root liner in 1986.

Disease: 'ZSFKF' has been free from disease, but the species has been reportedly susceptible to Dutch Elm Disease.

Pests: 'ZSFKF' has been free from serious pests, although Japanese Beetles will occasionally feed on new growth.

What is claimed is:

1. A new and distinct variety of Japanese *Zelkova* tree named 'ZSFKF' substantially as herein shown and described, characterized particularly as to novelty by its broad-spreading habit, more rapid growth rate, fibrous root system, and heat tolerance.

* * * * *